United States Patent [19]

Russ

[11] 4,044,604
[45] Aug. 30, 1977

[54] PORTABLE CONTAMINATED FUEL DETECTOR WITH TIERED DECK

[75] Inventor: Daniel G. Russ, Fort Wayne, Ind.

[73] Assignee: Telectro-Mek, Inc., Fort Wayne, Ind.

[21] Appl. No.: 696,273

[22] Filed: June 15, 1976

[51] Int. Cl.² .................. G01N 21/34; G01N 33/22
[52] U.S. Cl. ................................................ 73/61 R
[58] Field of Search ............... 73/61 R, 53; 356/51, 356/70, 201

[56] References Cited

U.S. PATENT DOCUMENTS

| | | | |
|---|---|---|---|
| 2,889,736 | 6/1959 | Borg | 73/61 R |
| 3,063,289 | 11/1962 | Moul | 73/61 R |
| 3,267,723 | 8/1966 | Robinson | 73/61 R |
| 3,308,649 | 3/1967 | Colechia | 73/61 R |

OTHER PUBLICATIONS

*Analysis and Control of Contamination in Aviation Fuels,* In Millipore Publ. pp. 13-14 & 17-18, Jan. 1968.

Primary Examiner—Richard C. Queisser
Assistant Examiner—Joseph W. Roskos
Attorney, Agent, or Firm—Dorfman, Herrell and Skillman

[57] ABSTRACT

A portable compact contaminated fuel detector is used with a standard batch sampling technique. The sample is passed through two series filters in a filter holder into a vacuum receptacle. The differential filter opacity is checked in a photocell fixture using a light whose intensity is first adjusted by a potentiometer to a standard level using a milliammeter which is also read to determine each filter opacity. The operating structure is carried on a tiered deck providing different horizontal levels for greater ease and facility in performing tests. The device is combinable with a free water detector, preferably within the enclosure provided by the deck and having an auxiliary movable closure through which the test procedure may be viewed. The free water detector includes a sample holder for filter sample in close proximity to a plurality of comparison standards representative of different water content levels against which the sample may be compared. An ultraviolet light source is positioned to illuminate a filter in the sample holder and comparison standards, the light being such as to cause chemicals in the filter subject to reaction with free water in a fuel sample passed therethrough, as well as the comparison standards, to fluoresce. The intensity of the sample fluorescence is a function of the amount of free water in a sample of standard size and the intensity of the comparison standards is fixed to represent that fluorescence which occurs with known concentrations of free water in a sample of that size.

7 Claims, 8 Drawing Figures

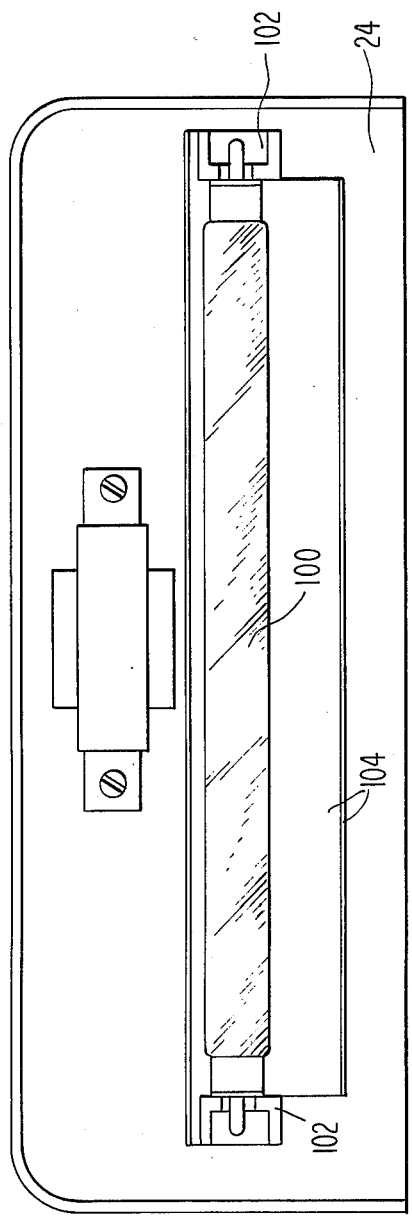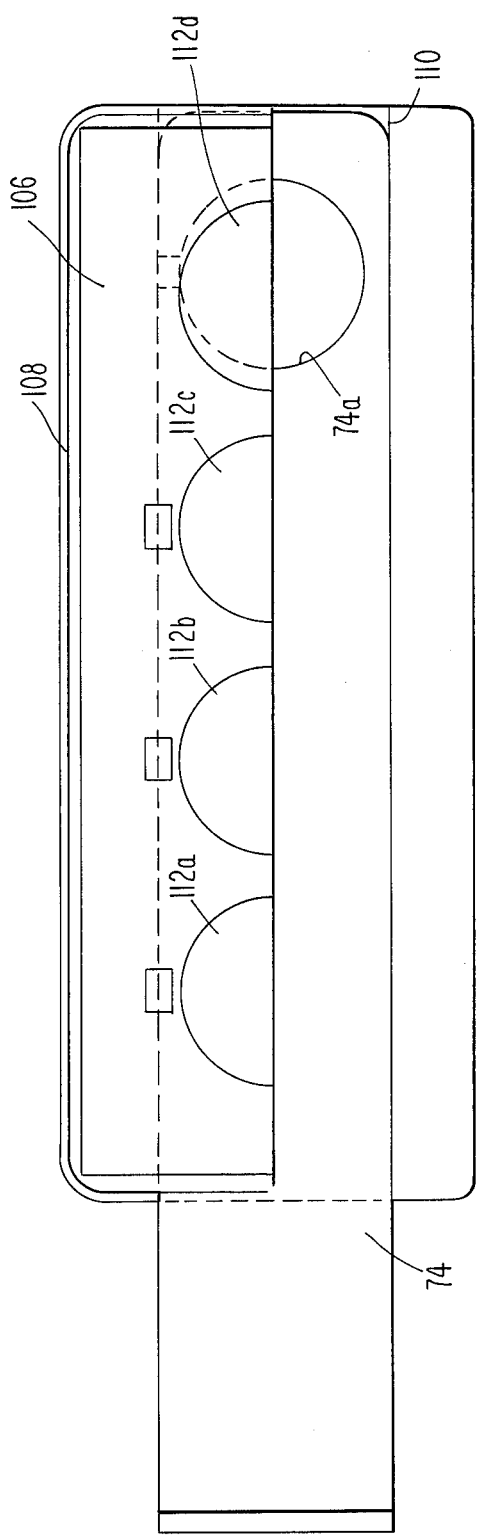

PORTABLE CONTAMINATED FUEL DETECTOR WITH TIERED DECK

The present invention concerns a portable contaminated fuel detector for use in checking fuel for contamination, particularly in places where portability is important. The detector is conveniently arranged on a tiered structure facilitating ease in handling and viewing. The detector can be made in such a way that danger of explosion is practically non-existent.

The practice of checking fuels for contamination has become increasingly important as fuels and engines become more sophisticated. Another system of my invention is described in my co-pending application entitled "Compact Portable Contaminated Fuel Detector with Hand-Operated Pump", U.S. patent application Ser. No. 671,309, filed Mar. 29, 1976. The preferred method of checking fuels for contamination employed by that system and this, and one described by Morton Moul in his U.S. Pat. No. 3,063,289 relies upon removal of the measured sample from a storage or use container so that it can be tested as a batch completely outside any system or process using the fuel. Such batch testing offers great advantages.

The present invention provides a portable contaminated fuel detector which is compact and easily used, an electrical cord and outlet for connection of the vacuum-pump motor and other electrical parts to available power lines. It provides a relatively uncomplicated structure which is arranged on a tiered deck which affords much convenient viewing of the parts which must be observed and more convenient handling of parts which must be manipulated without interference by other parts on other horizontal levels on the tiered deck.

The present invention also permits combination of a contaminated fuel detector with a free water detector to thereby provide in one piece of apparatus a capability of making two tests which are of great importance in connection with fuel safety. The free water detector involves the use of a filter including a chemical which varies in its intensity of fluorescence depending upon the amount of free water detected in a sample given batch size. The amount of fluoresense can be compared with standards whose fluorescent intensities represent known concentrations of free water in a sample of the same batch size. The free water detector is provided with untraviolet light means to cause fluorescence and the whole structure is preferably housed so as to prevent deterioration of the fluorescent materials but in such a way that the testing can be viewed. Viewing is also facilitated by the tiered construction of the deck on the box housing enclosure of the test set. The tiered construction readily lends itself to an auxiliary viewing opening which may be normally closed and opened during the test proceedings in order to view them and compare the intensity of fluorescence of sample and standards.

More specifically, the present invention represents an improvement in contaminated fuel detectors employing at least sample holder means, fuel filter means in a filter retainer, a vacuum receptacle arranged in series with means causing said parts to seal together upon drawing a vacuum to facilitate flow of fuel through the filter means into the vacuum receptacle and vacuum pump means for said purpose connected by a vacuum line to said vacuum receptacle. A box enclosure includes a top and a bottom. A tiered deck is supported on said bottom for supporting, in turn, a photosensor-filter examination system, including at least a light source, a filter holder and a photosensor, and a meter means coupled to said photosensor. The entrance to the vacuum receptacle includes a removable filter retainer. The top cover of the enclosure encloses parts projecting from the deck tiers and the tiers themselves which serve to provide a better view of all parts on display.

The tiered deck also facilitates the use of an included free water detector. The free water detector includes a sliding sample holder for a water filter pad sample in close proximity to a plurality of comparison standards representative of known free water concentration levels against which the sample may be compared. An ultraviolet light is provided which causes the filter subjected to free water from a specified fuel sample passed therethrough and comparison standards to fluoresce, the intensity of fluorescence of the sample filter being a function of the amount of free water. The sample holder is then positioned relative to comparison standards in order to make comparison of fluorescence of the standards and the sample possible. Each standard represents a predetermined and known free water concentration and the free water content of the fuel sampled is determined by visual comparison of the fluorescence of the chemically coated filter subjected to a specific quantity of fuel sampled with those of the standards provided.

For a better understanding of the present invention reference is made to the drawings, in which:

FIG. 7 is a sectional view taken along line 7—7 of FIG. 6; and

FIG. 8 is a sectional view taken along line 8—8 of FIG. 6.

Figure 1:
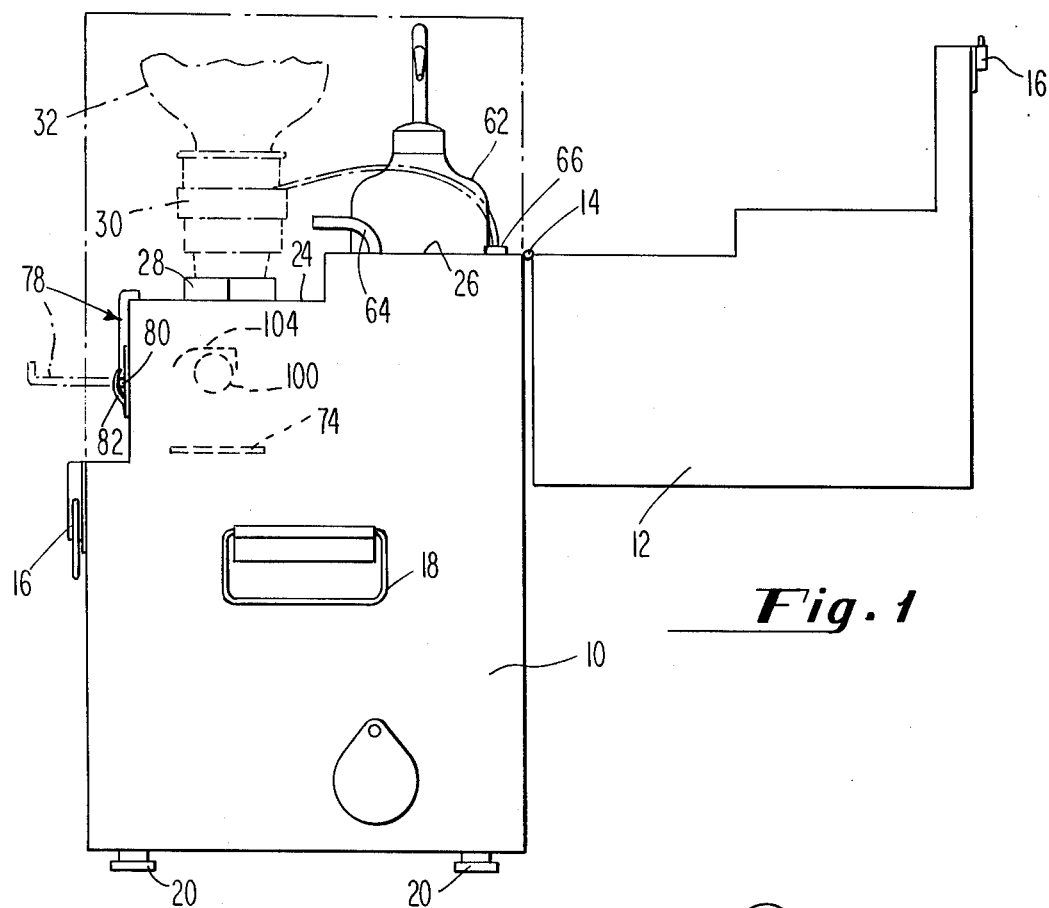
FIG. 1 is a side elevational view of the portable contaminated fuel and free water detector with the cover open, but showing closed cover position in dashed lines.
Figure 2:
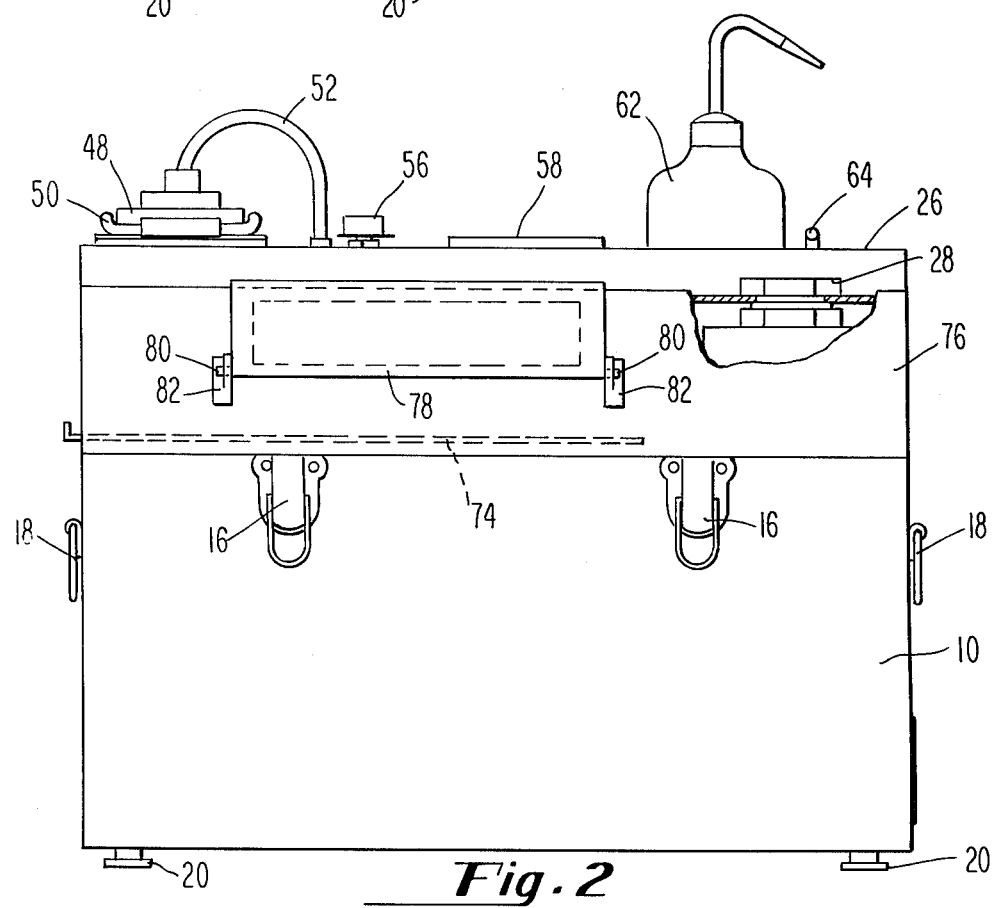
FIG. 2 is a front elevational view of the same structure showing structure attached to various decks.
Figure 3:
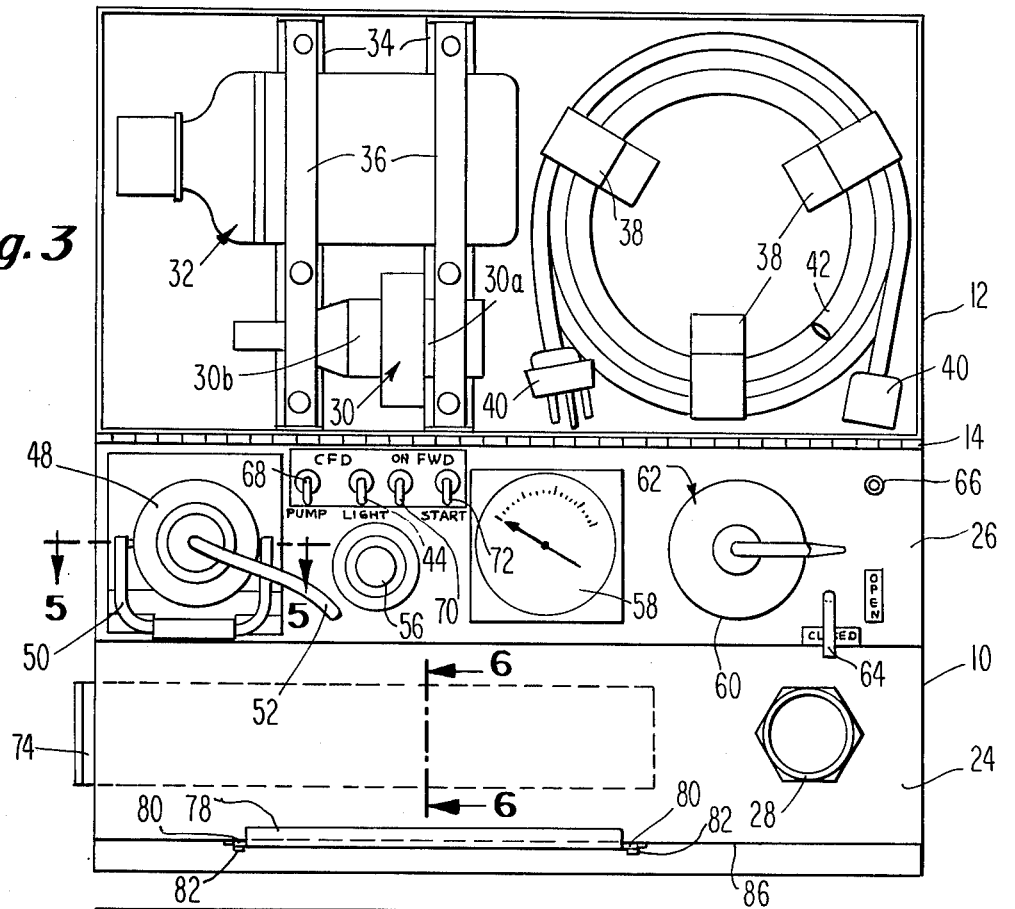
FIG. 3 is a plan view from above of the same structure.

Referring first to FIGS. 1, 2 and 3, it will be observed that a preferred embodiment of the contaminated fuel detector of the present invention is enclosed in a housing. The housing consists of a deep bottom box 10 to which a mating top cover 12 is connected at the back by hinge means 14 which permits closing of the cover 12 as shown in dashed lines, as seen in FIG. 1. The casing is preferably provided with a pair of manually operated toggle latches 16 which permit the top 12 and bottom 10 to be opened for use and firmly closed for carrying. Handles 18 are attached to the sides of box 10 to facilitate carrying. When the device is in use, it rests on four feet 20 attached to the bottom of the housing bottom box 10 and permitting the unit to be supported on a flat surface.

As seen in FIG. 1, the cover 12 closes the top opening of the box 10 which provides two support decks 24 and 26 at different horizontal levels. The depth of the box 10 is determined largely by the size of components of the system contained within it, described hereafter in connection with FIG. 4. The top cover 12 provides removable storage of parts and also accommodates parts projecting above the deck. This additional space is useful for storage of auxiliary equipment used in making tests, such as the sample bottle, electrical cord, tubing and other equipment.

Referring to FIG. 3, the point of view is one which would be seen by looking down from above into the open housing. The vacuum receptacle which is located principally below the deck 24 has a ring opening 28 which in turn receives the filter holder assembly 30 and the sample bottle 32, as shown schematically in dashed lines in FIG. 1. In FIG. 3, the filter holder assembly 30 and the sample bottle 32 rest in their storage cradle 34 held in place by straps 36 which are releasably snapped in place to secure the pieces as shown. Also stored in the cover 12 wrapped around suitable brackets 38 are an electrical power supply cord 40 and a hose 42.

Figure 4:
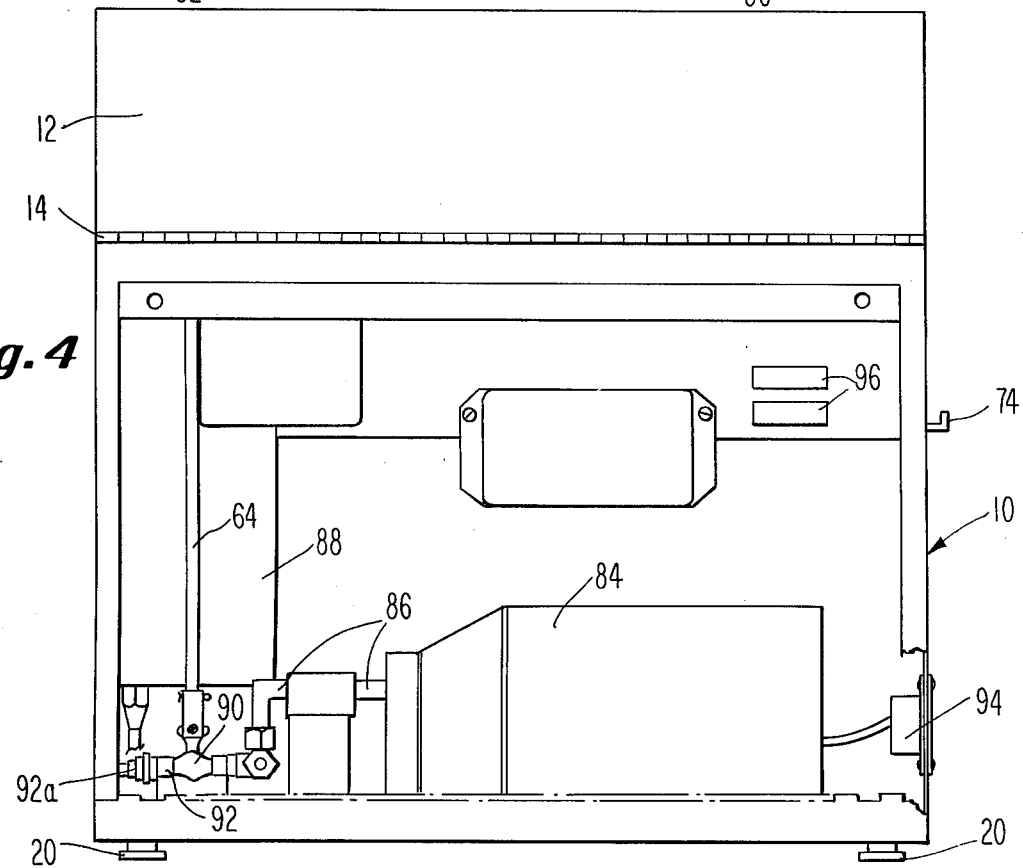
FIG. 4 is a back elevation view with the back panel removed.
Figure 5:
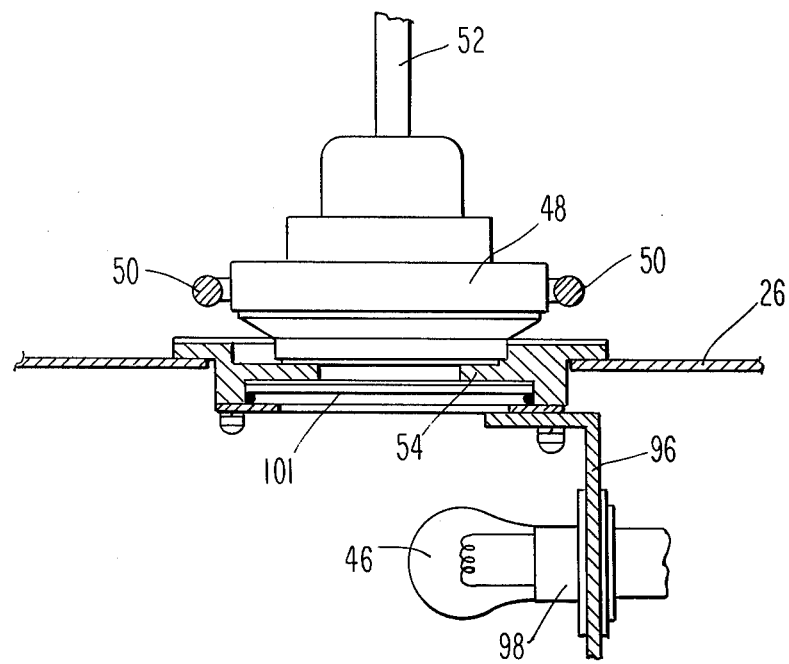
FIG. 5 is a sectional view taken along the line 5—5 of FIG. 3.

On the deck 26 is provided a light switch control 44 which turns on and off the light 46 (FIG. 5) associated with the photocell assembly 48 which is pivotally supported on the deck 26 by bracket 50 and connected into required electrical circuitry (not shown) beneath the deck cable 52. The light is directed to the photocell 48 through membrane filters held in filter holder 54 (FIG. 5). Intensity of the light 46 is regulated by a potentiometer and dial assembly 56 located on deck 26. The effect upon the photocell may be read on the milliammeter 58. In practice, for solid contamination determinations, the light intensity is set to a predetermined level on the milliammeter 58 by the adjustment of the potentiometer 56 prior to making measurements of the two filter opacities. Also in deck 26 is a well 60 for storing bottle 62 containing clean fuel for pre-wetting the filters. A valve conrol handle 64 closes and opens the drain in the vacuum receptacle 88 (FIG. 4) and a jack receptacle 66 receives a grounding plug attached to filter holder 30, during filtration processes. Other switch controls on the deck 26 grouped with switch control 44 include vacuum pump actuator switch control 68 and ultraviolet light on-off switch control 70 and start switch 72 for the fluorescent light control.

Figure 6:
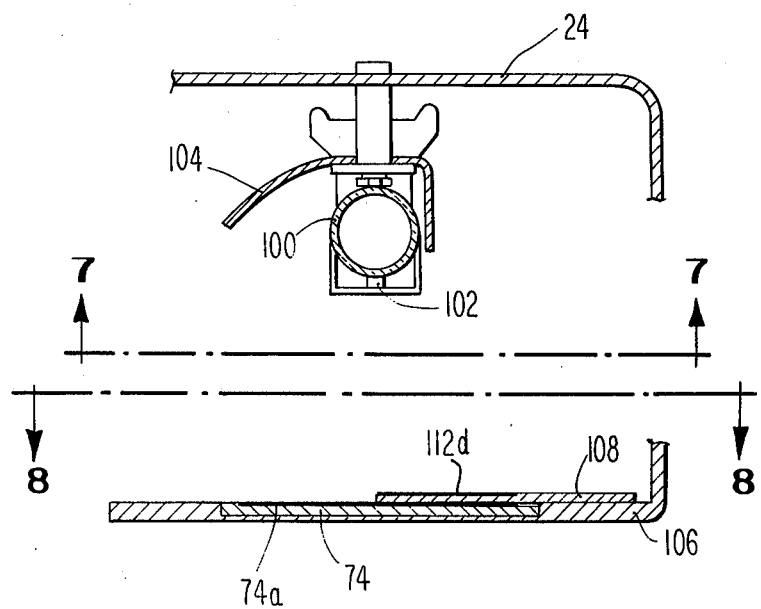
FIG. 6 is a sectional view taken along line 6—6 of FIG. 3.

Underneath deck 24 is the free water detector assembly shown in detail in FIGS. 6–8. After filtration of a specified fuel sample, the filter is supported therein on a movable slide 74, the upturned handling end of which is exposed and accessible even when the slide is fully inserted as seen in FIGS. 2, 3 and 4. The interior is viewed through an opening in the vertical wall 76 (FIG. 2), pivoting a spring-loaded cover closure 78 about square pins 80, as illustrated by the dashed line position shown in FIG. 1. The pins are supported against vertical deck 76 by spring brackets 82 which tend to cause pins 80 to assume stable positions with cover 78 against deck 76, either closed or open.

FIG. 4 shows an elevation view with the components beneath decks 24 and 26 in bottom 10 as viewed from the back with the back panel normally hinged at its bottom removed. The vacuum-pump assembly 84 which includes the actual vacuum-pump and explosion-proof drive motor is horizontally oriented and attached to the bottom of box 10 and connected by a suction line 86, permitting a vacuum to be drawn in the vacuum fuel receptacle 88 when the stopcock 90 controlled by handle 64 (FIG. 3) is in closed position. When the stopcock is in open position, the vacuum fuel receptacle 88 may be drained of fuel through line 92 which is provided with a conventional fitting 92a at its end to receive a drain hose 42 (FIG. 3). Hose 42 is removed from storage around brackets 38 in top 12, fed through a hole in the housing 10 and attached to fitting 92a. A shutter closure (not shown) is rotated about its pivot in housing 10 to permit exposure of the drain fitting 92a. The electrical line cord 40 (FIG. 3) is connected into receptacle 94 (FIG. 4) and to a power source.

Electrical circuitry is not shown, but it will be understood that it is conventional and that suitable wiring is provided in required circuitry to connect the power source through the fuses in fuse holders 96, the potentiometer 56 and the light 46, the vacuum-pump 84 through its switch 68 and the ultraviolet fluorescent lamp circuit of the free water detector and its switches 70 and 72 in conventional fashions. The light 46, shown in FIG. 5, is supported by bracket 96 below deck 26 in light socket 98.

As a practical matter, the light 46 is positioned below a glass 101 of filter holder 54 on top of which the filters are placed for light opacity detections, after filtration, in accordance with practice known in the art as taught by U.S. Pat. No. 3,063,289 to Morton Moul. The light passing through each filter detected by the photocell establishes a reading on milliammeter 46, and the differential current reading of the two series filters is then compared against a calibration to determine whether or not the solid fuel contamination level has reached or exceeded a predetermined rejection point, as is well-known practice in the prior art in accordance with the teaching of the aforesaid patent.

The filter holder 30 used for filtration of either solid or water contaminant samples is basically a hollow tubular member consisting of two parts 30a and 30b (FIG. 3) which are preferably easily fitted together by some sort of quick twist lock arrangement and between which in a flat screen support portion the two series filter under test (for solid contaminant detection) or one chemically treated water filter pad (for free water detection) are held so that all fuel in the sample must pass through them. For solid contamination detection, two filters are used together in series so that the first filter will catch any contamination and the second will simply be colored by the fuel. In this way, the differential measurements may be made to correct for the light opacity effects of fuel color when photocell measurements are taken. In this particular system, measurements are taken sequentially but in other systems simultaneous comparison of the filter might be made and arranged for direct readout of contamination.

FIG. 1 also shows the positioning of the fuel sample bottle 32 and filter holder 30 in use. The sample bottle has a level mark for measurement of a standard quantity of liquid, say, 800 ml. for solid contamination work and 500 ml. for free water work, by filling the bottle to the required mark. In practice, the filters are placed in position in the filter holder 30 and the filter holder is inserted over the neck of the bottle 32. Before the bottle and filter combination is put in place in receptacle 28, the drain handle 64 is turned to the closed position shutting the stopcock 90 and pump switch 68 is turned on allowing a vacuum to be drawn. Thereafter, this whole assembly is inverted and the tapered resilient tubular portion of the filter holder bottom 30b is inserted tightly in a sealing neck 28 of fuel receptacle 88, which completes a vacuum seal.

Referring now to FIGS. 6, 7 and 8, the structure of the free water detector is shown. Its location, as previously described, is under deck 24 and behind vertical deck 76 through which an opening is provided, closed by view cover 78, as previously described, which may be moved to the open position by rotation downward through 180° and stabilized there against vertical deck 76 because of the snap action of square pins 80 in spring 82 (FIGS. 1 and 2). In order to make the free water detection test, a special filter pad treated with a known chemical material which flouresces in proportion to the amount of free water detected in a sample is employed and its fluorescence under ultraviolet light, as a consequence of the amount of free water detected, can be compared with fixed standards whose fluorescence for such a sample exposed to the standard sized sample represent known levels of free water concentrations. As seen in FIG. 6, the structure is shown beneath deck 24 and consists of suitable fluorescent light with starting and operating circuitry (not shown) and supports for the conventional fluorescent ultraviolet light 100. The supports 102 at opposite ends are conventional and supported by brackets to the deck 24. Also provided is a reflector 104 which directs the ultraviolet light downward toward the sample and comparison standards, located respectively on standard support deck 106 and slide 74 (Figs. 2, 3 and 4). This standard support deck 106 is supported by a suitable sheet metal auxiliary support structure 108, which also supports guide means 110 in which slide member 74 slides horizontally and parallel to the length of the standard support deck 106. Supported on the standard support deck 106 are the successive standards 112a, 112b, 112c and 112d, which are positioned to overlie the slide effectively halfway and are semi-circular in form and about the size of the filter. The filter is placed in a filter receptacle 74a on slide 74 and by this positioning can be moved to positions opposed to each of the standards for direct comparison, or positioned between them to help in interpolation of the fluorescent intensity of the sample. Since the standards represent the fluorescence for known concentrations of free water in a sample of given size, the size being normally the volume of fuel passing through the chemically treated filter under test, the comparison of fluorescence tells the viewer the concentration of free water in the sample tested. Typically, the standards would represent the following quantities of free water in a 500 ml. sample:

Standard 112a, 0 parts per million free water;
Standard 112b, 5 parts per million free water;
Standard 112c, 10 parts per million free water;
Standard 112d, 20 parts per million free water.

In order to estimate the amount of free water when the standards are not exactly corresponding to the sample in intensity, it is possible to interpolate visually and obtain a figure of sufficient accuracy (usually 2 parts per million in the range above) for most purposes.

The flap 78 being repositionable in closed position helps preserve the accuracy of the standards by not exposing them excessively to light which tend gradually to deteriorate them. The standards are replaced periodically, in any event, to assure accuracy. The physical arrangement of the structure of the present invention makes it convenient to make the free water detection tests concurrently with a measurement of solid fuel contaminants using a single piece of apparatus for filtration of either sample volume (e.g. 800 ml. for solid contamination detection or 500 ml. for free water). The tiered structure of the decks makes it easier to perform tests of the different types at the same time with a minimum of inconvenience. The tiered arrangement makes it easier to see what is going on at different locations than the planar deck would. The tiered deck also permits the location of the flap and the view opening in the side in a way that can be conveniently closed when it is not in use.

The present invention has been described in terms of a preferred embodiment. Modifications of the invention within the scope of the appended claims will occur to those skilled in the art and are intended to be within the scope and spirit of the present invention.

I claim:

1. A combination contaminated fuel detector, comprising at least sample holder means, fuel filter means in a filter retainer, a vacuum receptacle arranged in series with means causing said parts to seal together upon drawing a vacuum to accelerate flow of fuel through the filter means into the vacuum receptacle and vacuum pump means for said purpose connected by a vacuum line to said vacuum receptacle, and a free water detector, comprising a sample holder for a filter sample in close proximity to a plurality of comparison standards representative of different water content levels against which the sample may be compared and a light source positioned to illuminate the sample holder and comparison standards and providing an ultraviolet light to cause chemicals in a treated filter pad subject to free water from a fuel sample passed therethrough and the comparison standards to fluoresce, the intensity of sample fluorescence being a function of the amount of free water, the improvement comprising combining the two detectors in a single unit and providing a box enclosure including a top and bottom, a tiered deck supported on said bottom for supporting, in turn, a photosensor filter examination system, including at least a light source, a filter holder and a photosensor and a meter means coupled to said photosensor, an entrance to the vacuum receptacle including a removable filter retainer, the top cover enclosing parts projecting above the deck tiers and the tiers serving to provide a better view of all parts on display, a slide element being insertable into the enclosure beneath, spaced from, and generally parallel to one of the tiered decks supported on a slide support to be positionable in sequence beside standards located proximate to the slide between the slide and the deck, a source of ultraviolet light being positioned beneath the deck and spaced above the sample holder and standards and a viewing opening being provided in a vertical connecting wall between the tiered deck region beneath which the slide is located and the lower deck element so as to be enclosed within the top cover.

2. The combined contaminated fuel and free water detector of claim 8 in which all elements but the entrance to the vacuum receptacle and removable filter retainer are on one tier and the vacuum receptacle and removable filter are on another to facilitate better viewing thereof.

3. The combined contaminated fuel and free water detector of claim 2 in which the photosensor filter examination system and meter together with switches for actuating a motor driving the pump and the photosensor system light source are on the highest tier of the deck and the entrance to the vacuum receptacle is on a lower tier.

4. The combined contaminated fuel and free water detector of claim 3 in which the slide for free water detector is located beneath an intermediate deck.

5. The combined contaminated fuel and free water detector of claim 4 in which the slide for the sample holder of the free water detector is introduced through a sidewall of the bottom of the box enclosure and movable past stationary standards on a deck which is stationary, close spaced to, and generally parallel to the slide so as to provide side-by-side comparison of the standards and the sample through the viewing opening in the sidewall when the ultraviolet light is illuminated.

6. The combined contaminated fuel and free water detector of claim 5 in which a movable cover is provided over the viewing opening which cover may be positioned to cover the opening or may be positioned away from the opening to permit viewing.

7. The combined contaminated fuel and free water detector of claim 6 in which the cover for the viewing opening is a sheet metal element rotatably supported on the vertical wall beneath said opening to permit rotation about said aligned pins to open and close the opening by moving the cover away from and back against the vertical deck in which the viewing opening occurs.

* * * * *

UNITED STATES PATENT OFFICE
CERTIFICATE OF CORRECTION

Patent No. 4,044,604            Dated August 30, 1977

Inventor(s) Daniel G. Russ

It is certified that error appears in the above-identified patent and that said Letters Patent are hereby corrected as shown below:

Column 3, line 34, "conrol" should be --control--;

Column 5, line 4, "spring" should be --springs--;

Claim 2, line 2, "8" should be --1--.

Signed and Sealed this

Seventh Day of February 1978

[SEAL]

Attest:

RUTH C. MASON          LUTRELLE F. PARKER
*Attesting Officer*         *Acting Commissioner of Patents and Trademarks*